United States Patent
Luo et al.

(10) Patent No.: US 11,781,974 B2
(45) Date of Patent: Oct. 10, 2023

(54) METHOD FOR DETECTING GAS CONCENTRATION IN GLASS BOTTLE WITH DYNAMICAL THRESHOLD ADJUSTMENT

(71) Applicant: CENTRAL SOUTH UNIVERSITY, Hunan (CN)

(72) Inventors: Qiwu Luo, Hunan (CN); Mingyang Zhu, Hunan (CN); Chunhua Yang, Hunan (CN); Zihuai Liu, Hunan (CN); Weihua Gui, Hunan (CN)

(73) Assignee: CENTRAL SOUTH UNIVERSITY, Changsha (CN)

( * ) Notice: Subject to any disclaimer, the term of this patent is extended or adjusted under 35 U.S.C. 154(b) by 233 days.

(21) Appl. No.: 17/421,087

(22) PCT Filed: Jul. 13, 2020

(86) PCT No.: PCT/CN2020/101574
§ 371 (c)(1),
(2) Date: Jul. 7, 2021

(87) PCT Pub. No.: WO2021/008476
PCT Pub. Date: Jan. 21, 2021

(65) Prior Publication Data
US 2022/0107264 A1  Apr. 7, 2022

(30) Foreign Application Priority Data

Jul. 17, 2019  (CN) .......................... 201910644523.2

(51) Int. Cl.
*G01N 21/31* (2006.01)
*G01N 21/84* (2006.01)
*G01N 33/00* (2006.01)

(52) U.S. Cl.
CPC ............ *G01N 21/31* (2013.01); *G01N 21/84* (2013.01); *G01N 33/0036* (2013.01)

(58) Field of Classification Search
CPC .... G01N 21/31; G01N 21/84; G01N 33/0036; G01N 2021/936; G01N 21/90;
(Continued)

(56) References Cited

U.S. PATENT DOCUMENTS 6,097,428 A    8/2000 Wu et al.
2019/0195789 A1*  6/2019 Pan .......................... G01N 21/39

FOREIGN PATENT DOCUMENTS

CN    103163102 A    6/2013
CN    107643252 A    1/2018
(Continued)

OTHER PUBLICATIONS

International Search Report issued by the China National Intellectual Property Administration for corresponding International Patent Application No. PCT/CN2020/101574, dated Oct. 14, 2020, with an English translation.

*Primary Examiner* — Tarifur R Chowdhury
*Assistant Examiner* — Akbar Hassan Rizvi
(74) *Attorney, Agent, or Firm* — Myers Wolin, LLC (57) ABSTRACT

A method for detecting gas concentration in a glass bottle with dynamical threshold adjustment is provided includes acquiring second harmonic peaks $P_0$, $P_a$, $P_X$ in the glass bottle, calculating absolute values of the differences between $P_0$ and $P_a$, as well as between $P_0$ and $P_X$, and performing quality inspection on a glass bottle to be detected. The performing includes collecting the second harmonic peaks for the glass bottle to be detected, calculating a mean $P_L$ of elements in the current queue L, updating the second harmonic peak $P_a$ and the second harmonic peak $P_X$, collecting second harmonic peaks for a current glass bottle to be
(Continued)

detected, and determining whether the current glass bottle to be detected is an acceptable medicinal bottle based on the updated data and the collected second harmonic peaks.

6 Claims, 4 Drawing Sheets

(58) Field of Classification Search
CPC ...... G01N 21/93; G01N 21/25; G01N 21/255; G01J 3/433
See application file for complete search history.

(56) References Cited

FOREIGN PATENT DOCUMENTS

| | | |
|---|---|---|
| CN | 109540806 A | 3/2019 |
| CN | 109738392 A | 5/2019 |
| CN | 110286093 A | 9/2019 |
| WO | 2018/156004 A1 | 8/2018 |

* cited by examiner

METHOD FOR DETECTING GAS
CONCENTRATION IN GLASS BOTTLE
WITH DYNAMICAL THRESHOLD
ADJUSTMENT

CROSS-REFERENCE TO RELATED APPLICATION

This application is a National Phase of PCT/CN2020/101574, filed on Jul. 13, 2020, and which designated the U.S., which claims priority to Chinese Patent Application No. 201910644523.2, filed on Jul. 17, 2019. The contents of each are wholly incorporated herein by reference.

CROSS REFERENCE TO RELATED APPLICATION

The present disclosure claims priority of the Chinese patent application titled "METHOD FOR DETECTING GAS CONCENTRATION IN GLASS BOTTLE WITH DYNAMICAL THRESHOLD ADJUSTMENT" and filed to CNIPA (National Intellectual Property Administration of PRC) on Jul. 17, 2019 with the application number of 201910644523.2, which is entirely incorporated herein by reference.

TECHNICAL FIELD

The present disclosure relates to the technical field of gas detection, and particularly to a method for detecting gas concentration in a glass bottle with dynamical threshold adjustment, which identifies whether the glass bottle is acceptable or not through dynamically adaptive gas concentration detection based on a threshold.

BACKGROUND ART

In the pharmaceutical industry, some international companies, such as LIGHTHOUSE Company in the United States and Belletti Company in Italy, have applied the wavelength modulation spectroscopy (WMS) technology to oxygen concentration detection in sealed medicinal glass bottles. However, due to influences of the optical noise caused by the glass bottle wall, the system instrument noise, the nonlinear intensity modulation, and temperature and humidity in random free spaces, the second harmonic signal extracted by the WMS technology shows fluctuation in background, which in turn affects the accuracy and stability of concentration measurement. Therefore, eliminating the influence of background fluctuation is the core of improving concentration measurement and medicinal glass bottle acceptance examination.

Currently in the area of real-time background-deducting nonlinear correction of a spectrum, Werle et al. put forward a method for collecting the spectral line signal of the background gas first and then the spectral line absorption signal of the target gas for deduction. Persson et al. improved the structure of a light path gas chamber and carried out nonlinear processing to reduce the influence of baseline. However, the above-mentioned methods are only suitable for systems equipped with gas absorption cells; while technical methods disclosed by LIGHTHOUSE, Belletti and other companies need to add standard bottles at intervals on the pharmaceutical production line to detect background noise on the production line so as to deduct the noise. However, extra standard bottles arranged reduce the production capacity of the production line, and the background noise obtained in advance is different from that of the medicinal bottles under testing due to the time difference. Therefore, it is necessary to research a method for gas concentration detection in self-adaptive threshold medicinal glass bottles without standard bottles.

SUMMARY

The present disclosure aims at providing a method for detecting gas concentration in a glass bottle with dynamical threshold adjustment, which identifies whether the glass bottle is acceptable or not through gas concentration detection performed by dynamical and adaptive threshold adjustment. This method is a glass bottle acceptance examination means which is simpler in operation and higher in real-time performance, and effectively reduces or eliminates background interference. This method has no need to add standard bottles into a production line, and it is not limited to application within a system equipped with a gas absorption cell, which means it can realize high-precision detection in an open environment.

The present disclosure provides a method for detecting gas concentration in a glass bottle with dynamical threshold adjustment, including:

Step 1: an acceptable concentration threshold a % and a reference concentration auxiliary threshold X % of a target gas in a glass bottle are acquired, and by using the wavelength modulation spectroscopy (WMS) detection method in the current environment, second harmonic peaks $P_0$, $P_a$, $P_X$ in the glass bottle are respectively acquired under the concentrations of 0%, a %, X %, wherein 0%<X %<a %;

Step 2: an absolute value is calculated for the difference between the second harmonic peaks $P_0$ and $P_a$ to get $D_a$, and an absolute value is calculated for the difference between the second harmonic peaks $P_0$ and $P_X$ to get $D_x$;

Step 3: quality inspection is performed for the glass bottle to be detected on the basis of the difference $D_a$ and $D_x$ in Step 2 as follows:

Step 31: the second harmonic peaks are collected for the glass bottle to be detected in order to determine whether the peaks are less than or equal to the second harmonic peak $P_a$ under the acceptable concentration threshold a %, and, if so, the glass bottle to be detected is an acceptable medicinal bottle and the process proceeds to Step S32, otherwise the glass bottle is unacceptable and the detection is performed on the next glass bottle to be detected;

Step 32: it is determined whether the second harmonic peaks of the glass bottle to be detected are less than or equal to the second harmonic peak $P_X$ under the reference concentration auxiliary threshold X %, and, if so, the second harmonic peaks of the glass bottle to be detected are sequentially added into a queue L;

Wherein the queue L has a length of M, and the first element in the initial queue L is equal to the second harmonic peak $P_0$ while the rest of the elements are null; and when the queue is full, for adding new elements, old elements are sequentially discarded;

Step 33: a mean $P_L$ of elements in the current queue L is calculated, and the second harmonic peak $P_a$ under the acceptable concentration threshold a % is updated with the sum of the mean $P_L$ and the difference $D_a$, and the second harmonic peak $P_X$ under the reference concentration auxiliary threshold X % is updated with the sum of the mean $P_L$ and the difference $D_x$, wherein the updated data is used to detect the next glass bottle to be detected following Steps S31-S33.

The present disclosure is based on the priori condition that most glass bottles in the actual production line are acceptable and a target gas concentration of the glass bottles is 0%, and in the current production environment, by averaging the second harmonic peaks in the second harmonic peak range which are filtered in real time in adjacent times and meet the reference concentration auxiliary threshold X %, a dynamic second harmonic peak $P_L$ of the reference concentration is obtained so as to replace the function of traditional on-line detection of 0% standard sample bottles in the production line. Since the second harmonic peak $P_L$ is obtain by using the adjacent time data, which implies current background interference factors, the second harmonic peak $P_a$ of the acceptable concentration threshold a % and the second harmonic peak $P_X$ of the reference concentration auxiliary threshold X % are dynamically updated by using the second harmonic peak $P_L$ of the reference concentration value. Finally, the second harmonic peak $P_a$ of the updated acceptable concentration threshold a % is used to identify whether the current glass bottle is accepted or not, and the current background interference factors implied in the second harmonic peak $P_a$ of the updated acceptable concentration threshold a % are offset with the background interference existing in the second harmonic peak of the current glass bottle, thereby effectively eliminating the background interference existing in the second harmonic peak corresponding to the current glass bottle, and reducing or eliminating the interference of environmental factors in real time to improve the glass bottle detection accuracy. It should be understood that the obtained $P_0$, $P_a$, $P_X$ and subsequent detection of the glass bottle in the present disclosure are preferably carried out in the same detection environment. However, there are differences in environmental interference at different times in the same detection environment. In the present disclosure, the background interference is eliminated by using the data of adjacent times, which assumes that the difference is small between background interferences in adjacent times.

More preferably, the acceptable concentration threshold a % is 5%, and the reference concentration auxiliary threshold X % is 1%.

More preferably, the length M of the queue L is determined according to the moving speed of a glass bottle to be detected in the production line, and the faster the speed is, the greater the length M will be.

More preferably, when the moving speed is 200-600 bottles/min, the value range of length M is [15,35].

More preferably, when updating elements in the queue L, the old elements are discarded by the first-in-first-out rule.

The element that enters the queue first is arranged at the head of the queue, and the rest of the elements that enter the queue afterward are arranged in sequence; the queue should meet the first-in-first-out rule, that is, when the queue is full, if there are more elements to join the queue, the element at the head of the queue will overflow automatically.

The target gas is oxygen, and the glass bottle is a medicinal glass bottle.

Advantageous Effects

1. According to the present disclosure, a queue L with a fixed length M is set, and elements in the queue L are dynamically updated according to the second harmonic peaks in the second harmonic peak range which are filtered in real time and meet the reference concentration auxiliary threshold X %. Therefore, for the current moment, as the background interference shows little change in a short time, the second harmonic peak of dynamic reference concentration obtained by calculating the average value of elements in the queue L implies the current background interference factors. In addition, according to the present disclosure, in any background, as the real-time environmental change and the influence of air have been deducted from the differences $D_a$ and $D_x$, the second harmonic peak $P_a$ of the acceptable concentration threshold a % and the second harmonic peak $P_X$ of the reference concentration auxiliary threshold X % that are dynamically updated by using the differences $D_a$, $D_x$ and the second harmonic peak $P_L$ of the reference concentration imply current background interference factors, and thus when the second harmonic peak $P_a$ of the dynamically updated acceptable concentration threshold a % is used to identify whether the current glass bottle is accepted or not, the second harmonic peak may be offset with the background interference factors existing in the second harmonic peak of the current glass bottle, thereby effectively eliminating the background interference existing in the second harmonic peak corresponding to the current glass bottle, and reducing or eliminating the interference of environmental factors in real time to improve the glass bottle detection accuracy.

2. The detection method provided by the present disclosure is simpler in operation and higher in real-time performance, which enables dynamic update by using real-time data, and eliminates errors caused by environmental fluctuations accurately in real time; moreover, the method does not need a system equipped with a gas absorption cell, and may reflect environmental changes in real time in an open target gas environment, thus better meeting requirements of the actual industrial line.

3. The reliability of the detection method provided by the present disclosure is also verified by experiments in the present disclosure.

DETAILED DESCRIPTION OF THE EMBODIMENTS

The present disclosure will be further described with reference to embodiments below.

The present disclosure provides a method for detecting gas concentration in a glass bottle with dynamical threshold adjustment is used for the target gas concentration detection in the glass bottle, wherein the glass bottle is deemed unacceptable when the target gas concentration in the glass bottle exceeds a set standard, and it is regarded as an unqualified glass bottle, whereby particularly the second harmonic peak is used as a comparative feature to identify whether the glass bottle is acceptable or not. The present disclosure is mainly used for detecting the medicinal glass bottle with oxygen being the target gas. In the detection disclosed in the present disclosure, by averaging the second harmonic peaks in the second harmonic peak range which are filtered in real time in adjacent times and meet the reference concentration auxiliary threshold X %, a dynamic second harmonic peak $P_L$ of the reference concentration is obtained, which is associated with current environment so as to replace the function of traditional on-line detection of 0% standard sample bottles in the production line. In addition, the second harmonic peak $P_a$ of the acceptable concentration threshold a % and the second harmonic peak $P_X$ of the reference concentration auxiliary threshold X % are dynamically updated by using the second harmonic peak $P_L$ of the reference concentration value. Compared with the second harmonic peak $P_a$ of a fixed acceptable concentration threshold a % in the traditional detection method, the second harmonic peak $P_a$ of the acceptable concentration threshold a % in the method provided in the present disclosure dynamically varies with the fluctuation of current environmental interference. When the second harmonic peak is used to detect the quality of the current glass bottle in real time, the environmental interference between two peaks may be offset so as to achieve a better match between the detected result and the real result. In the same way, the second harmonic peak $P_X$ of the reference concentration auxiliary threshold X % also dynamically varies with the fluctuation of current environmental interference. Therefore, the queue updated by the second harmonic peak is more consistent with the current environment, and finally the reliability of the second harmonic peak $P_L$ of reference concentration is improved, thus forming a dynamically changing determination criterion consistent with the current environment.

Figure 1:
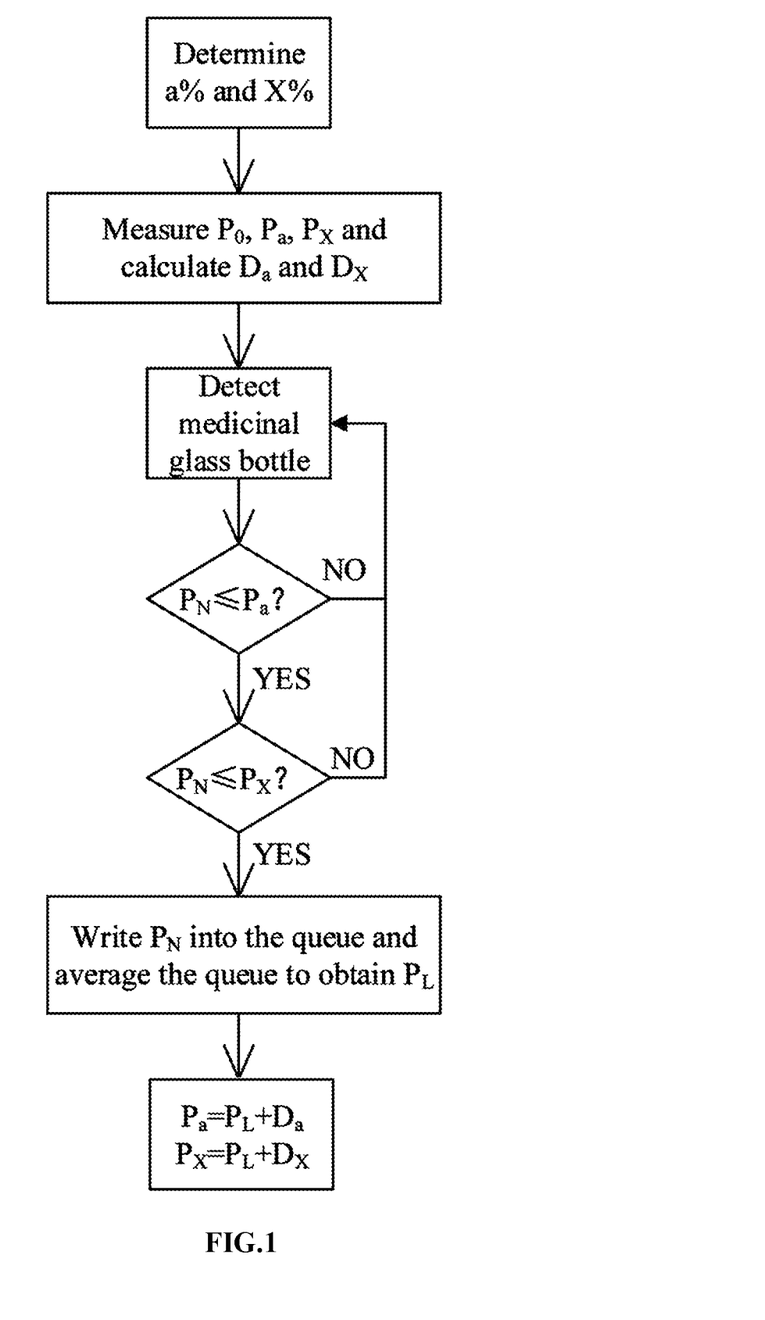
FIG. 1 is a schematic flowchart of a method for detecting gas concentration in a glass bottle with dynamical threshold adjustment provided by embodiments in the present disclosure.

As shown in FIG. 1, the embodiment in the present disclosure provides a method for detecting gas concentration in a glass bottle with dynamical threshold adjustment, which mainly applies to the detection in the medicinal glass bottle with oxygen being the target gas, including:

Step 1: an acceptable concentration threshold a % and a reference concentration auxiliary threshold X % of a remaining oxygen amount in a medicinal glass bottle are acquired, and by using the wavelength modulation spectroscopy (WMS) detection method in the same environment, second harmonic peaks $P_0$, $P_a$, $P_X$ in the medicinal glass bottle are respectively acquired under the concentrations of 0%, a %, X %, wherein 0%<X %<a %. In the present disclosure, the acceptable concentration threshold a %=5% and the reference concentration auxiliary threshold X %=1% are preferred, and in other feasible embodiments, the acceptable concentration threshold a % and the reference concentration auxiliary threshold X % are set according to requirements of actual production and detection. It is to be noted that the medicinal glass bottle in this embodiment is sealed and measured in the air.

Step 2: an absolute value is calculated for the difference between the second harmonic peaks $P_0$ and $P_a$ to get $D_a$, and an absolute value is calculated for the difference between the second harmonic peaks $P_0$ and $P_X$ to get $D_x$. $D_a=P_a-P_0$, $D_x=P_X-P_0$, wherein in any background or environment, the differences $D_a$ and $D_x$ both keep unchanged as the real-time environmental change and the influence of air have been deducted from the difference equation.

Step 3: quality inspection is performed for the medicinal glass bottle to be detected in the production line on the basis of the differences $D_a$ and $D_x$ in Step 2, wherein the following steps are repeated for an individual medicinal glass bottle in the production line:

Step 31: the second harmonic peaks $P_N$ are collected for the medicinal glass bottle to be detected in order to determine whether the peaks are less than or equal to the second harmonic peak $P_a$ under the acceptable concentration threshold a % (it is determined if $P_N \leq P_a$?); and, if so, the medicinal glass bottle to be detected is an acceptable medicinal bottle and the process proceeds to Step S32, otherwise the glass bottle is unacceptable and the detection is performed on the next medicinal glass bottle to be detected;

Step 32: it is determined whether the second harmonic peaks of the medicinal glass bottle to be detected are less than or equal to the second harmonic peak $P_X$ under the reference concentration auxiliary threshold X % (it is determined if $P_N \leq P_X$?); and, if so, the second harmonic peaks of the medicinal glass bottle to be detected are sequentially added into a queue L;

Wherein the queue L has a length of M, and the first element in the initial queue L is equal to the second harmonic peak $P_0$ while the rest of the elements are null; for adding new elements, old elements are sequentially discarded, that is, the element that enters the queue first is arranged at the head of the queue, and the rest of the elements that enter the queue afterward are arranged in sequence; and the queue should meet the first-in-first-out rule, that is, when the queue is full, if there are more elements to join the queue, the element at the head of the queue will overflow automatically.

Step 33: a mean $P_L$ of elements in the current queue L is calculated, and the second harmonic peak $P_a$ under the acceptable concentration threshold a % is updated with the sum of the mean $P_L$ and the difference $D_a$ such that $P_a=P_L+D_a$, and the second harmonic peak $P_X$ under the reference concentration auxiliary threshold X % is updated with the sum of the mean $P_L$ and the difference $D_x$ such that $P_X=P_L+D_x$, wherein the updated data is used to detect the next medicinal glass bottle to be detected following Steps S31-S33.

In order to verify the reliability of the present disclosure, the acceptable concentration threshold a %=5% and the reference concentration auxiliary threshold X %=1% are selected in Embodiment 1, and the second harmonic peaks of the standard sample bottles of 5%, 1% and 0% under laser irradiation are collected, which are: $P_5=5$, $P_1=1$, and $P_0=0$, therefore $D_a=P_5-P_0=5$, $D_x=P_1-P_0=1$. In an experimental environment, 100 sealed medicinal glass bottles are successively measured which include 10 standard medicinal glass bottles with an oxygen concentration of 4% and 10 standard medicinal glass bottles with an oxygen concentration of 6%. The measured data is processed by the algorithm in the related art and the method of this embodiment respectively to obtain the data as shown in FIG. 2.

For Algorithm 1 in the related art: regardless of the environmental influence on the second harmonic peaks of the medicinal bottles in the production line, that is, when a=5 is set, a constant invariant $P_5=5$ is used as the basis for whether the medicinal bottles are acceptable or not, wherein the auxiliary threshold is $P_5=5$.

In this embodiment: the method for using the dynamic threshold disclosed in the present disclosure is adopted, wherein the dynamic threshold $P_5$ is dynamically updated.

Figure 2:
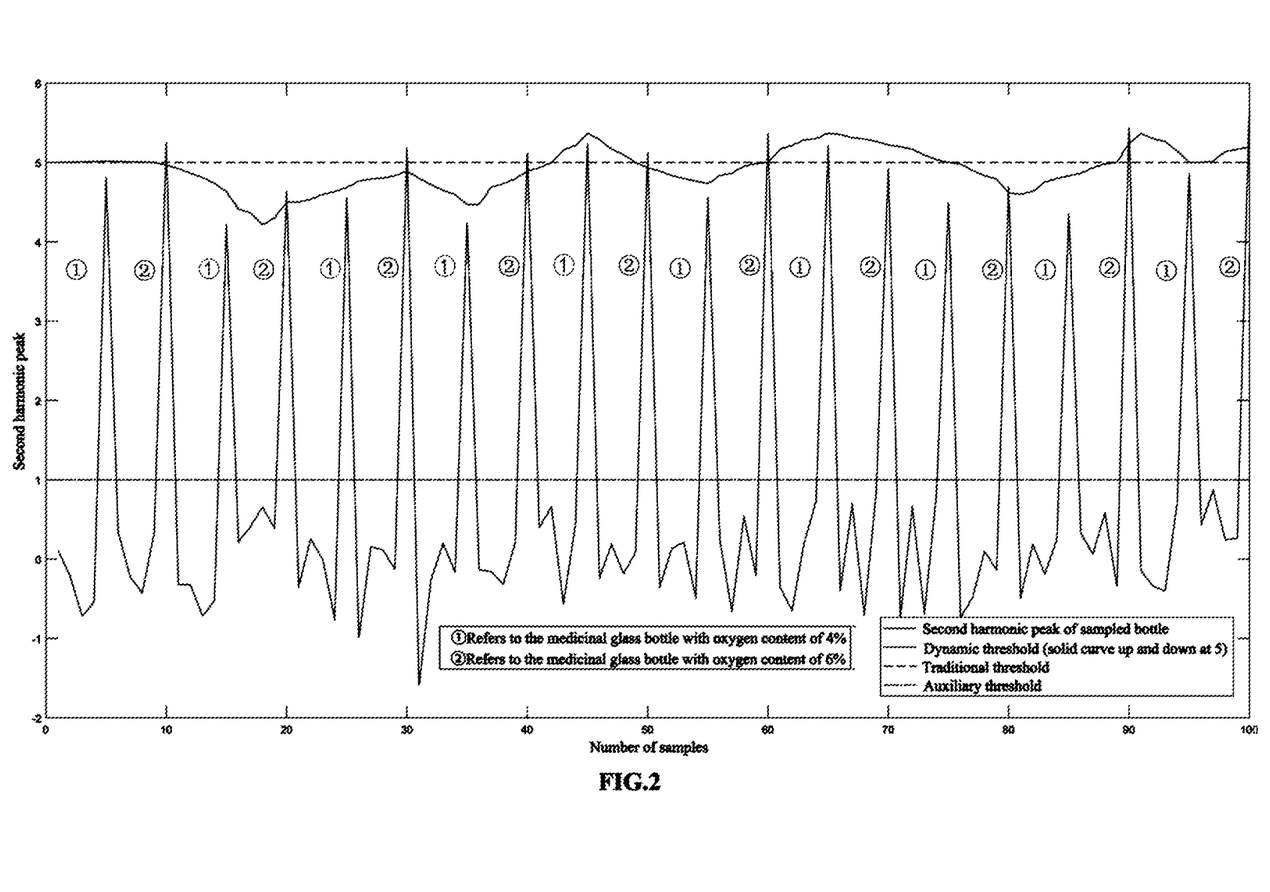
FIG. 2 is a data comparison diagram between the embodiment 1 of the present disclosure and the algorithm in the related art.

As shown in FIG. 2, if the constant invariant $P_5=5$ in the algorithm in the related art is used as the basis for whether the medicinal bottles are acceptable or not, the second harmonic peaks corresponding to the 45th and 65th standard medicinal glass bottles with an oxygen concentration of 4% rise due to the environmental interference and are larger than $P_5=5$, resulting in that the 45th and 65th medicinal bottles are misidentified as unacceptable medicinal bottles. The second harmonic peaks corresponding to the 20th and 80th standard medicinal glass bottles with an oxygen concentration of 6% decrease due to the environmental interference and are less than $P_5=5$, resulting in that the 20th and 80th medicinal bottles are misidentified as acceptable medicinal bottles. After using the method of the embodiment, the dynamic threshold will change with the environment, so that the second harmonic peaks corresponding to the 45th and 65th standard medicinal glass bottles with an oxygen concentration of 4% rise due to the environmental interference but are still less than $P_5=5$, and thus the 45th and 65th medicinal bottles will not be misidentified as unacceptable medicinal bottles. The second harmonic peaks corresponding to the 20th and 80th standard medicinal glass bottles with an oxygen concentration of 6% decrease due to the environmental interference but are still larger than $P_5=5$, and thus the 20th and 80th medicinal bottles will not be misidentified as acceptable medicinal bottles.

Embodiment 2

In this embodiment, the oxygen concentration threshold of the acceptable medicinal bottles is determined as a %=5% and a threshold is set to X %=1%. In the background of the current environment, the second harmonic peaks of the standard sample bottles of 5%, 1%, and 0% under laser irradiation are collected to obtain corresponding second harmonic peaks $P_5=0.99433$, $P_1=0.99146$, and $P_0=0.99050$. Then, the absolute values are calculate for the differences of two groups of second harmonic peaks between $P_0$ and $P_a$, and between $P_0$ and $P_X$, so as to obtain $D_a=0.00383$ and $D_x=0.00096$, wherein the length M of the queue L is selected as 15. Then the medicinal glass bottles are detected according to the above steps S31-S33. In an actual production line, 999 sealed medicinal glass bottles are successively measured which include 4 standard medicinal glass bottles with an oxygen concentration of 4% and 3 standard medicinal glass bottles with an oxygen concentration of 6%. The measured data is processed by the algorithm in the related art and the method of this embodiment respectively to obtain the data as shown in FIG. 3 and FIG. 4.

For Algorithm 1 in the related art: regardless of the environmental influence on the second harmonic peaks of the medicinal bottles in the production line, that is, when it is set a=5, an invariant $P_5=0.99433$ is used as the basis for whether the medicinal bottles are acceptable or not.

In this embodiment: the method for using the dynamic threshold disclosed in the present disclosure is adopted, wherein the dynamic threshold $P_5$ is dynamically updated.

Figure 3:
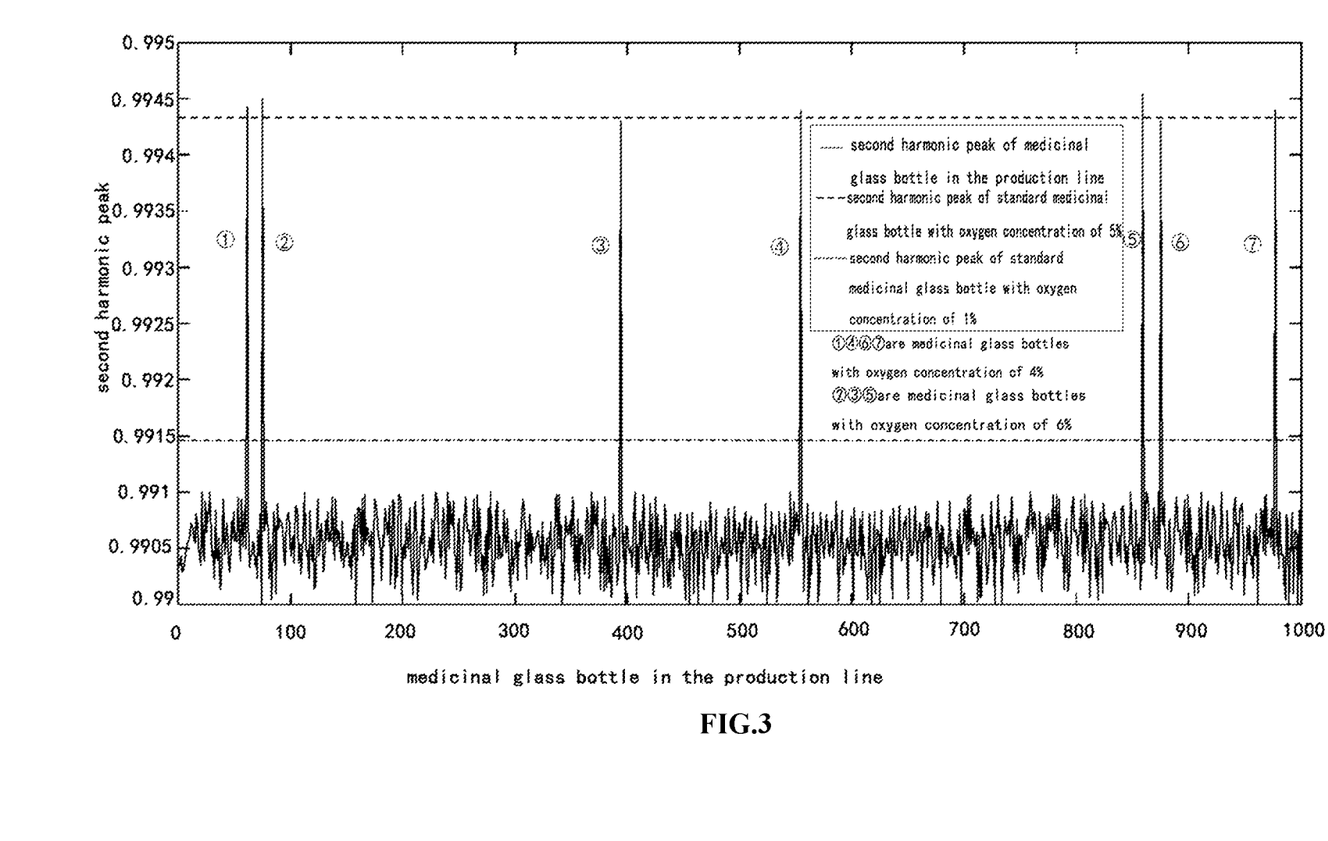
FIG. 3 is a data schematic view of the algorithm in the related art according to the present disclosure.
Figure 4:
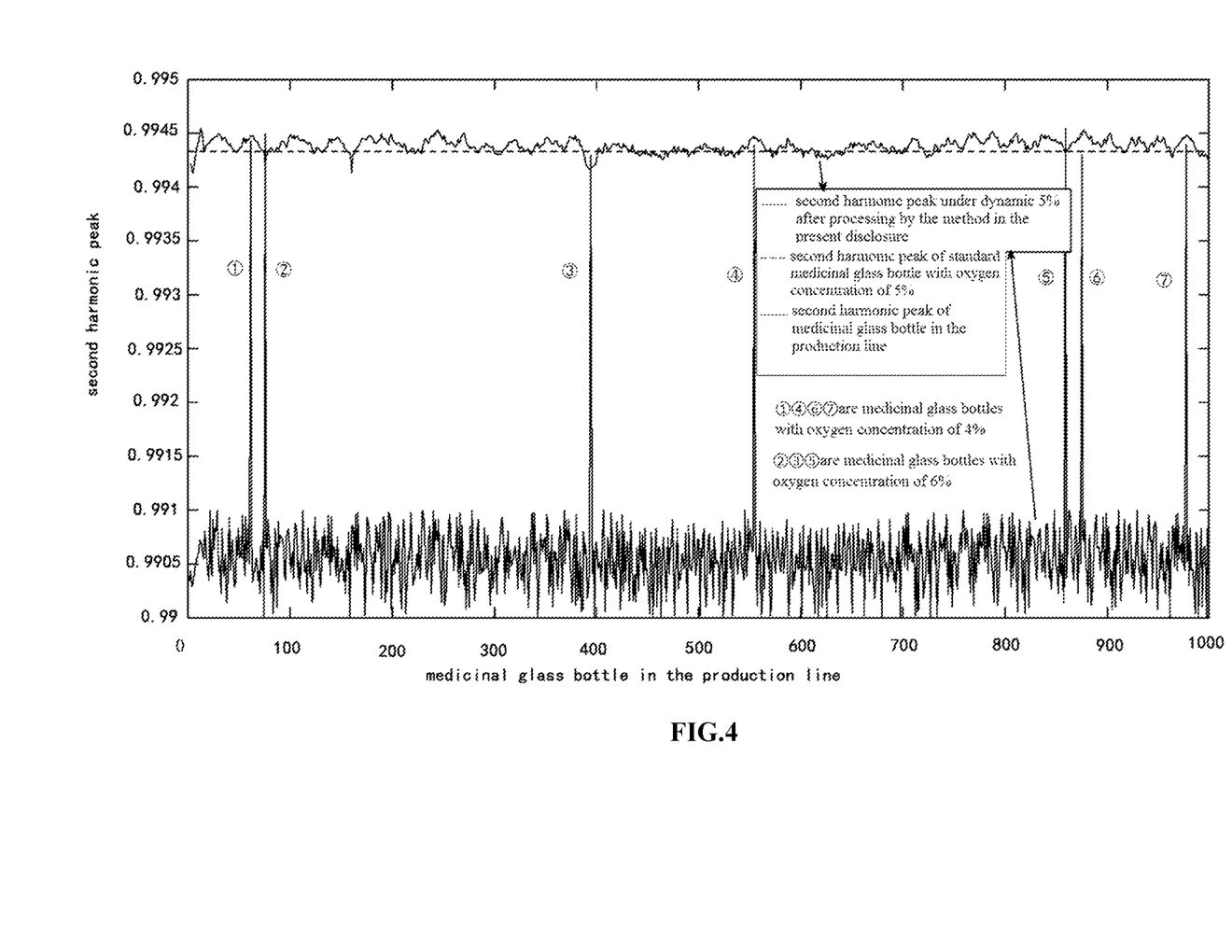
FIG. 4 is a data schematic view of the embodiment 2 of the present disclosure.

FIG. 3 shows the data obtained by using Algorithm 1 in the related art, wherein the second harmonic peak $P_5=0.99433$ is measured for a standard medicinal bottle with an oxygen concentration of 5% in the current environment. After the processing of standard medicinal glass bottles ①④⑥⑦ and ②③⑤ with oxygen concentrations of 4% and 6% respectively by Algorithm 1, the second harmonic peaks $P_①=0.99443$, $P_④=0.99441$, and $P_⑦=0.99442$ corresponding to the standard medicinal glass bottles ①④⑦ with the oxygen concentration of 4% rise due to the environmental interference and $P_①$, $P_④$, and $P_⑦$ are greater than $P_5=0.99433$, resulting in that the medicinal bottles ①④⑦ are misidentified as unacceptable medicinal bottles, while the second harmonic peak $P_3=0.99430$ corresponding to the standard medicinal glass bottle ③ with the oxygen concentration of 6% decreases due to the environmental interference and $P_③=0.99430<P_5=0.99433$. Given the above results, Algorithm 1 in the related art will lead to false determination of the system, and acceptable medicinal bottles will be misidentified as unaccepted by the system under the environmental interference, and those unaccepted medicinal bottles may also be misidentified as acceptable. As shown in FIG. 4, it is measured in the current environment that the second harmonic peaks of the standard medicinal bottles with oxygen concentrations 5%, 1%, and 0% are $P_5=0.99433$, $P_1=0.99146$, and $P_0=0.99050$, respectively. After the processing of standard medicinal glass bottles ①④⑥⑦ and ②③⑤ with oxygen concentrations of 4% and 6% respectively by using the detection method in this embodiment, the second harmonic peaks $P_①=0.99443$, $P_④=0.99441$, and $P_⑦=0.99442$ corresponding to the standard medicinal glass bottles ①④⑦ with the oxygen concentration of 4% rise due to the environmental interference but $P_①$, $P_④$, and $P_⑦$ are still less than $P_5$, so that the medicinal bottles ①④⑦ will not be misidentified as unacceptable medicinal bottles, while the second harmonic peak $P_③=0.99430$ corresponding to the standard medicinal glass bottle ③ with the oxygen concentration of 6% decreases due to the environmental interference but $P_③=0.99430>P_5$, so that the medicinal bottle ③ will not be misidentified as acceptable medicinal bottle.

It can be seen from the comparison of the above results between Embodiment 1 and Embodiment 2 that the dynamic threshold $P_5$ of the method provided in the present disclosure changes with the environment, and thus when it is used as the determination criterion, it may instead greatly reduce or eliminate the interference of environmental factors and improve the detection lower limit of residual oxygen within medicinal glass bottles.

It should be noted that the examples described in the present disclosure are illustrative but not restrictive, so the present disclosure is not limited to the examples described in the specific implementations. Any other implementations obtained by those skilled in the art according to the technical scheme of the present disclosure, no matter modified or replaced, all fall within the protection scope of the present disclosure as long as they do not deviate from the purpose and scope thereof.

What is claimed is:

1. A method for detecting gas concentration in a glass bottle with dynamical threshold adjustment, comprising:
   acquiring an acceptable concentration threshold a % and a reference concentration auxiliary threshold X % of a target gas in a glass bottle, and acquiring second harmonic peaks $P_0$, $P_a$, $P_X$ in the glass bottle respectively under the concentrations of 0%, a %, X % by using a wavelength modulation spectroscopy (WMS) detection method in a current environment, wherein 0%<X %<a %;
   calculating an absolute value for a difference between the second harmonic peaks $P_0$ and $P_a$ to get $D_a$, and calculating an absolute value for a difference between the second harmonic peaks $P_0$ and $P_X$ to get $D_x$;
   performing quality inspection on a glass bottle to be detected based on the differences $D_a$ and $D_x$ in the calculating as follows:
   collecting the second harmonic peaks for the glass bottle to be detected by using the WMS detection method in order to determine whether the peaks are less than or equal to the second harmonic peak $P_a$ under the acceptable concentration threshold a %, and, if so, the glass bottle to be detected is an acceptable medicinal bottle and the process proceeds to determining whether the second harmonic peak, otherwise the glass bottle is unacceptable and the detection is performed on a next glass bottle to be detected;
   determining whether the second harmonic peaks of the glass bottle to be detected are less than or equal to the second harmonic peak $P_X$ under the reference concentration auxiliary threshold X %, and, if so, the second harmonic peaks of the glass bottle to be detected are sequentially added into a queue L;

wherein the queue L has a length of M, and the first element in the initial queue L is equal to the second harmonic peak $P_0$ while the rest of the elements are null; and for adding new elements, old elements are sequentially discarded;

calculating a mean $P_L$ of elements in the current queue L, and updating the second harmonic peak $P_a$ under the acceptable concentration threshold a % with the sum of the mean $P_L$ and the difference $D_a$, and updating the second harmonic peak $P_X$ under the reference concentration auxiliary threshold X % with the sum of the mean $P_L$ and the difference $D_x$;

collecting second harmonic peaks for a current glass bottle to be detected by using the WMS detection method; and determining whether the current glass bottle to be detected is an acceptable medicinal bottle based on the collected second harmonic peaks for the current glass bottle to be detected, the updated second harmonic peak $P_a$, and the u dated second harmonic peak $P_X$.

2. The method according to claim 1, wherein: the acceptable concentration threshold a % is 5%, and the reference concentration auxiliary threshold X % is 1%.

3. The method according to claim 1, wherein: the length M of the queue L is determined according to a moving speed of a glass bottle to be detected in the production line, and the faster the speed is, the greater the length M will be.

4. The method according to claim 3, wherein: when the moving speed is 200-600 bottles/min, the value range of the length M is [15,35].

5. The method according to claim 1, wherein: during the updating of elements in the queue L, old elements are discarded by a first-in-first-out rule.

6. The method according to claim 1, wherein: the target gas is oxygen, and the glass bottle is a pharmaceutical glass vial.

* * * * *